US00PP36887P2

(12) United States Plant Patent
Hansen

(10) Patent No.: US PP36,887 P2
(45) Date of Patent: Aug. 12, 2025

(54) ***HOSTA* PLANT NAMED 'Leaving Me Breathless'**

(50) Latin Name: ***Hosta* hybrid (Tratt.)**
Varietal Denomination: Leaving Me Breathless

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,378

(22) Filed: Dec. 20, 2024

(51) Int. Cl.
*A01H 5/02* (2018.01)
*A01H 5/12* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02; A01H 5/12
See application file for complete search history.

*Primary Examiner* — Kent L Bell

(57) ABSTRACT

A new and distinct *Hosta* plant named 'Leaving Me Breathless' produces medium-sized low mounds. The foliage is in basal rosettes, broadly ovate, leaves with long narrowly acute apices, cordate bases and slightly wavy margins. The leaves are variegated having bluish-green margins and pale-yellow to creamy white centers with intermediate color separation between the margin and center of variably large segments of several shades of chartreuse. The medium-sized leaves have a glaucous matte top and bottom. The broadly campanulate flowers are pale purple with white edges appearing beginning in mid-July. Each flower is attractively subtended by a floral bract that mimics the leaf variegation making the scape showy for long periods. 'Leaving Me Breathless' is useful in the landscape, as a container plant, a specimen or en masse.

2 Drawing Sheets

Botanical classification: *Hosta* hybrid (Tratt.).
Variety denomination: 'Leaving Me Breathless'.

STATEMENT REGARDING PRIOR DISCLOSURES UNDER 37 CFR 1.77 (b) (6)

*Hosta* 'Leaving Me Breathless' was first introduced by the inventor as a non-enabling description in registration of the name in early 2024 with the International Cultivar Registration Authority for the genus *Hosta*. No plants of *Hosta* 'Leaving Me Breathless' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Leaving Me Breathless' hereinafter also referred to as the new plant or by the cultivar name, 'Leaving Me Breathless'. *Hosta* 'Leaving Me Breathless' was hybridized by the inventor on Jul. 6, 2015, at a wholesale perennial nursery in Zeeland, Michigan, USA. The female parent was the proprietary unreleased hybrid known only as 11-206-2 (not patented) and the male parent was the proprietary unreleased hybrid known only as 11-55-1 (not patented). The seeds from this cross were planted in February of 2016 and a single seedling selection from this cross eventually produced the new plant. The new plant was assigned the breeder code 15-177-1 and passed the initial evaluation in the summer of 2016. 'Leaving Me Breathless' has been asexually propagated by division at the same nursery since 2023 and also by careful shoot tip plant tissue culture with the resultant asexually propagated plants having retained all the same traits as the original plant. *Hosta* 'Leaving Me Breathless' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Angel Falls' U.S. Plant Pat. No. 28,785, 'American Sweetheart' (not patented), 'Cool As a Cucumber' (not patented), 'Lakeside Love Affair' (not patented), 'Lakeside Paisley Print' (not patented), 'Love Story' U.S. Plant Pat. No. 34,224, 'Miss America' U.S. Plant Pat. No. 32,068, 'Sea Thunder' (not patented), 'Viva Las Vegas' (not patented), and 'When I Dream' U.S. Plant Pat. No. 34,284.

The habit of 'Angel Falls' is more arching in habit with a more greenish-yellow leaf center earlier in the season and slightly more vein pairs, the leaf margin is green and more sinuate to undulate, and the flowers are more flared. 'American Sweetheart' has thicker and stiffer foliage and more upright habit, and the leaves have a wider green margin and narrower center with less intermediate variegated colors between the margin and center. 'Cool As a Cucumber' has a larger, longer, more lanceolate, and more arching foliage with a green margin and whiter center, and the scapes are upright. 'Lakeside Love Affair' has foliage that is shorter and more broadly ovate with less intermediate colors between the margin and center variegation. 'Lakeside Paisley Print' has a stiffer and thicker substance foliage with broader more sinuate green margins and narrower center variegation, the scapes become more lavender blushed, and the flowers are darker purple. 'Love Story' has a smaller habit with longer foliage, the leaves are smoother and less bullate. 'Miss America' has a larger habit, stiffer and thicker foliage with broader green margins and narrower variegated leaf center, and the flowers are larger, open wider, with a darker lavender center stripe, and the scapes are larger and upright. 'Sea Thunder' has smaller habit and smaller foliage with less intermediate colors between the green margin and center, the flowers are dark lavender and the scape is larger and more upright. 'Viva Las Vegas' has a larger habit with larger foliage that is broader, less bullate, less sinuate, and the center color is more white and the margin is green. 'When I Dream' is larger in habit and leaf size, the foliage has a more white center, and the scapes are upright.

The female parent is larger and taller with cordate leaves and streaked variegation thinly spread out in sectors throughout the leaves rather than with the lighter sector all being confined to the middle of the leaves, and the scape is more upright. The male parent larger and more horizontal habit with solid bluish-green colored foliage, and the scapes are arching to horizontal.

Other *Hosta* cultivars may have individual traits similar to 'Leaving Me Breathless' but the new plant differs from the above listed cultivars and all other *Hostas* known to the applicant, by the combination of the following traits.

1. Leaves are medium-sized, broadly ovate, with narrowly acute apices and cordate bases;
2. Leaves have a slightly wavy margin and have slightly impressed adaxial veins;
3. Leaf margins are bluish-green and centers color is pale yellow to creamy white with intermediate color separation between the margin and center of variably large segments of several shades of chartreuse;
4. Broadly campanulate flowers are pale purple with white edges well above the foliage on arching to outwardly creamy-colored scapes beginning in mid-July;
5. Flowers are densely arranged on scapes with the first flowers beginning to open well above the foliage;
6. Floral bracts subtend each flower have a variegation that mimics the foliage;
7. The habit is a medium-sized low mound.

BRIEF DESCRIPTION OF THE DRAWING

The photographs of the new plant demonstrate the overall appearance of the new plant, including the unique traits. The colors are as accurate as reasonably possible with color reproductions. Ambient light spectrum, temperature, source and direction may cause the appearance of minor variations in color.

The drawings show an eight-year-old 'Leaving Me Breathless' plant in a trial garden at a nursery in Zeeland, MI with supplement fertilizer and water as needed.

DETAILED BOTANICAL DESCRIPTION

Figure 1:
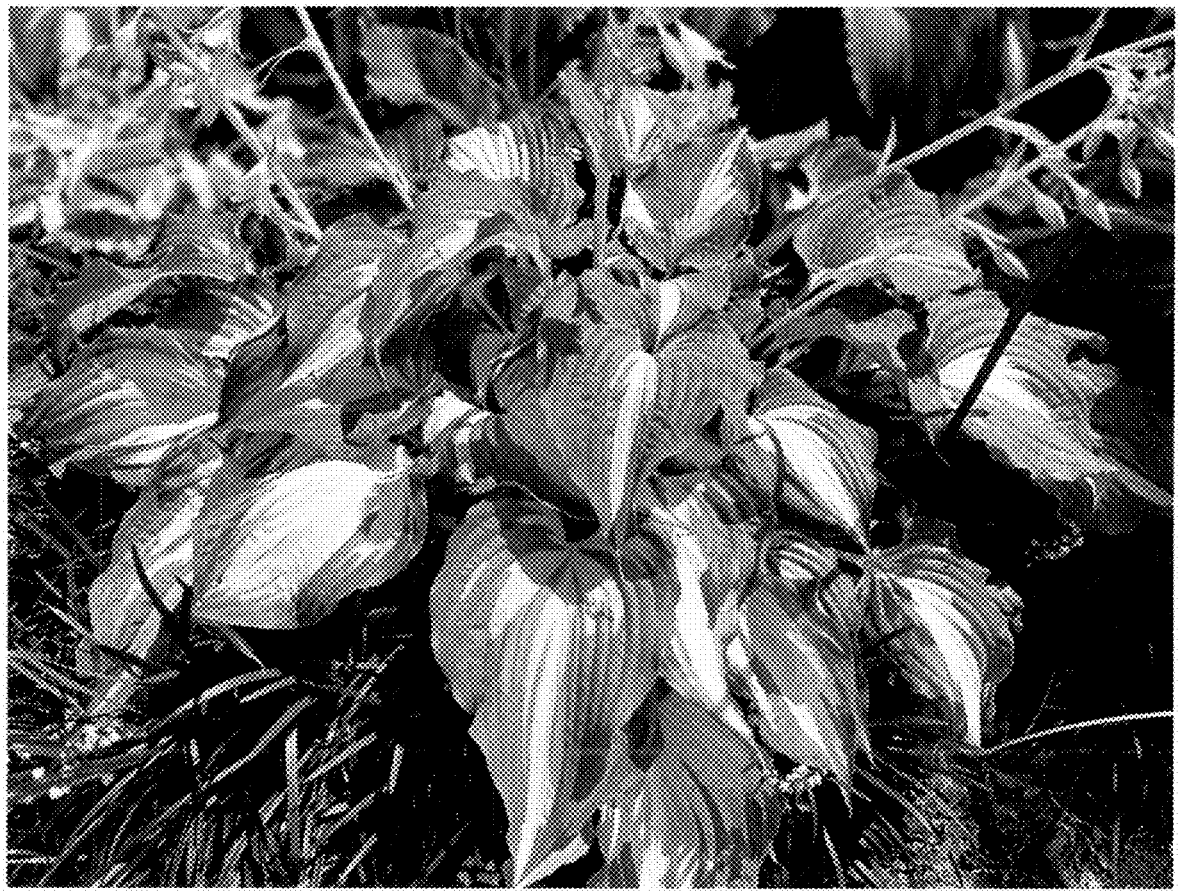
FIG. 1 shows the landscape foliage habit of a new plant in early flowering stage.
Figure 2:
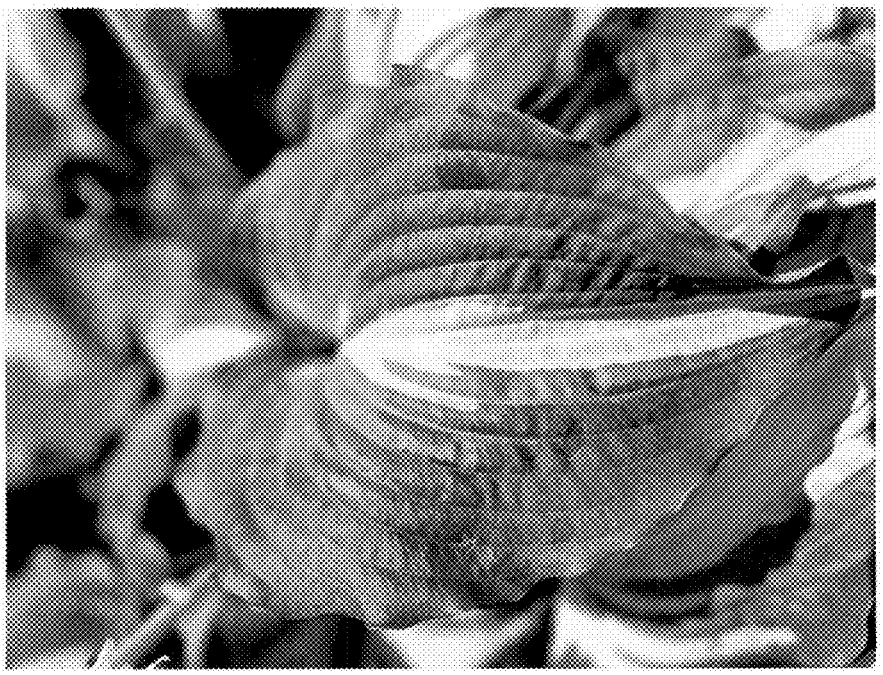
FIG. 2 shows a close-up of a leaf.
Figure 3:
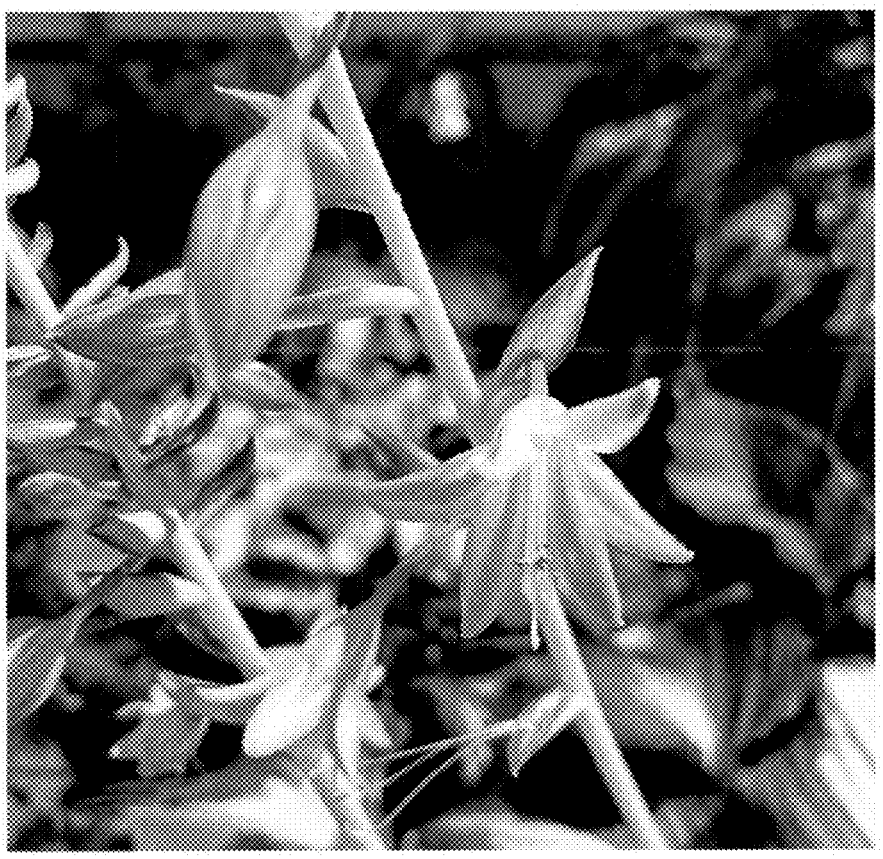
FIG. 3 shows a close-up of the flower, buds and foliar bracts.

The following descriptions and color references are based on the 2015 edition of The Royal Horticultural Society Colour Chart except where common dictionary terms are used. The new plant, *Hosta* 'Leaving Me Breathless', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of an eight-year-old plant in a shaded trial garden in Zeeland, Michigan with supplemental water and fertilizer.

Botanical classification: *Hosta* x hybrid;

Parentage: Female or seed parent is 11-206-2; male or pollen parent is 11-55-1;

Propagation: Garden division and sterile shoot tip tissue culture;

Time to initiate roots from tissue culture: About three weeks;

Growth rate: Moderately vigorous to slow;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a low medium-sized mound of outwardly extending petioles and leaves and arching scapes flowering above foliage;

Plant size: Foliage height to about 45 cm above soil line to the top of the leaves, to about 68 cm tall to the top of the flowers and to about 118 cm wide at the widest point just above the soil line;

Foliage description: Broadly ovate; narrowly acute apex, cordate base; margin entire, and slightly sinuate; slightly folded; flat and not bullate between the veins, glabrous and smooth both surfaces; flexible; variegated;

Leaf blade size: To about 33 cm long and about 20 cm wide about one-third way from the base;

Leaf blade color: early season and expanding adaxial margin nearest RHS N138B, center between RHS 138B and RHS 146B; abaxial early season and expanding margin between RHS 191B and RHS N138D, center between RHS 191B, RHS 191C, and RHS 147C; mid-season and mature adaxial margin between RHS NN137A and RHS 139A, center between RHS 160C and RHS 150D, with intermediate zone comprising colors of between RHS N144A and RHS 146A, between RHS 145A and RHS 146B, and nearest RHS 137B; abaxial mid-season and mature margin between RHS 190A and RHS NN138B, center nearest RHS 160D, with intermediate zone comprising colors of between RHS 191B and RHS 191C, between RHS 193B and RHS 191C, and nearest RHS 191D;

Veins: 11 to 12 pairs with midrib; slightly impressed adaxial and costate and smooth abaxial;

Vein color: Young adaxial margin region nearest RHS N138B and center nearest RHS 146D, young abaxial margin region nearest RHS N138B and center nearest RHS 148C; mature adaxial margin nearest RHS 146A, and center nearest RHS 160D, mature abaxial margin nearest RHS 137B and center nearest RHS 160D;

Petiole: Glabrous and matte both adaxial and abaxial; moderately concavo-convex; stiff; to 40 cm long and 10 mm wide at base and about 5 mm deep;

Petiole color: Adaxial margin nearest RHS 138A, center nearest RHS 157D with random longitudinal streaks close to margin of between RHS 145B and RHS 145C; abaxial margin nearest RHS 138A, inside portion nearest RHS 4D and region surrounding midrib nearest RHS 157D;

Flower description—

Buds one to two days prior to opening: Clavate with acute apex and narrow tube and rounded base; about 47 mm long and 1 mm in diameter at the widest portion in the bulb, tube to about 15 mm long and to about 3 mm diameter at base, quickly tapering from bulb;

Bud color: Distal tube and proximal half of bulb between RHS 76C and RHS 85C with apical half of bulb and proximal half of tube between RHS 76B and RHS 85B;

Flowers: Perfect; incomplete; broadly campanulate; attitude outwardly to slightly downwardly; to 62 mm long to exserted pistil; corolla to 50 mm long and 45 mm wide at apex, fused in basal 34 mm, free in the distal 22 mm, decreasing in size distally; corolla tube portion 15 mm long and quickly tapering to 3 mm diameter in middle; with rounded base; flowers tightly arranged on scape;

Flowering lasting: Persists for a normal period, usually about one day on plant;

Flowering period: Scapes remain effective with flowers beginning mid-July for about three weeks; with about 40 flowers per scape; mostly secund;

Fragrance: No detectable fragrance;

Tepal: Two sets of three; clavate; entire margins; acute apex; fused in basal 34 mm; glabrous adaxial and abaxial; outer set to about 12 mm wide and 57 mm long; inner set to about 13 mm wide and 57 mm long;

Tepal color: Outer set adaxial nearest RHS 76B in the longitudinal center and nearest RHS NN155D along the margins and the corolla tube, abaxial between RHS 85C and RHS 76C in the bulb and nearest RHS 85C on the corolla tube; inner set adaxial nearest RHS 76B in the longitudinal center and nearest RHS NN155D along the margins and corolla tube, abaxial between RHS 85C and RHS 76C in the bulb and nearest RHS 85C on the corolla tube; both sets with a transparent 0.5 mm to 1 mm wide margin;

Gynoecium: Single; to about 66 mm long; superior;

*Style*.—Cylindrical; glabrous; to about 57 mm long and 0.7 mm diameter; straight with distal 10 mm arcuate upwards 90°; color nearest RHS 155A.

*Stigma*.—Globose; puberulent; about 1 mm long and 1 mm diameter; color nearest RHS NN155A.

*Ovary*.—Ellipsoidal; superior; apex rounded; base rounded to truncate; sides deeply furrowed, about 8 mm long and 2.5 mm diameter; color between RHS 145A and RHS N144A.

Androecium: Six;

*Filaments*.—Six; cylindrical; approximately 60 mm long and 0.5 mm in diameter; curved or bent upwardly about 90° in the distal 10 mm; color nearest RHS NN155B.

*Anthers*.—Oblong with rounded ends; basifixed, longitudinally dehiscent; about 5 mm long and 2 mm wide when fully developed in unopened flower; color adaxial a mottling of nearest RHS N77C, RHS 11D, and RHS NN155A, abaxial blend between RHS N77C and RHS NN155A.

*Pollen*.—Sparse; spherical; less than 0.1 mm long; color nearest RHS 12A.

Peduncle: Cylindrical; usually one per mature division; about 4 per plant; glabrous; moderately glaucous; aspect arching to outwardly; to about 78 cm long, and about 6 mm in diameter at base, average about 68 cm long and 5 mm diameter at base;

Inflorescence: Flowering portion about 30 cm long and 7 cm wide; with variegated bracts subtending each flower;

Peduncle color: Nearest RHS 157C;

Pedicel: Cylindrical; glabrous; slightly lustrous; to about 19 mm long and 2 mm diameter; mostly straight; attitude outwardly;

Pedicel color: Nearest RHS 85A;

Bracts: Typically three below first flower and one subtending each flower; lanceolate; narrowly acute apex and truncate base and clasping; entire margin; glabrous and slightly glaucous abaxial and adaxial; to about 31 mm long 16 mm wide, decreasing distally; variegated margin about 2 mm to 4 mm wide;

Bract color: At flowering adaxial margin nearest RHS 146A, center nearest RHS NN155B, with an intermediate zone comprising nearest RHS 146D, RHS 145A and between RHS N144D and RHS 145D; abaxial margin nearest RHS 147A, center nearest RHS 155B with an intermediate zone comprising RHS 147B and RHS 146B, abaxial with a faint blush of nearest RHS N79B in random locations;

Fruit: Rare; three-valved dehiscent capsule; to about 2.5 cm long and 3 to 4 mm diameter; color at maturity nearest RHS 164C;

Seeds: Not yet observed;

Disease resistance: Resistance and susceptibility to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8.

It is claimed:

1. A new and distinct *Hosta* plant named 'Leaving Me Breathless' as herein described and illustrated.

* * * * *